(12) United States Patent
Rasmussen et al.

(10) Patent No.: US 8,092,516 B2
(45) Date of Patent: Jan. 10, 2012

(54) STENT MEMBER

(75) Inventors: Erik Rasmussen, Slagelse (DK); Kim Moegelvang Jensen, Koebenhavn SV (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/613,836

(22) Filed: Nov. 6, 2009

(65) Prior Publication Data

US 2010/0114294 A1     May 6, 2010

(30) Foreign Application Priority Data

Nov. 6, 2008    (GB) .................................. 0820360.6

(51) Int. Cl.
    *A61F 2/06*         (2006.01)
(52) U.S. Cl. ...................... 623/1.16; 623/1.15; 623/1.13
(58) Field of Classification Search .......... 623/1.15–1.16, 623/1.3–1.31
See application file for complete search history.

(56) References Cited

U.S. PATENT DOCUMENTS

| | | | |
|---|---|---|---|
| 5,938,697 A * | 8/1999 | Killion et al. ................. | 623/1.15 |
| 6,027,525 A * | 2/2000 | Suh et al. ....................... | 623/1.1 |
| 6,709,453 B2 | 3/2004 | Pinchasik et al. | |
| 6,723,119 B2 | 4/2004 | Pinchasik et al. | |
| 6,926,734 B1 * | 8/2005 | Klein ............................ | 623/1.34 |
| 2002/0013617 A1 * | 1/2002 | Matsutani et al. ........... | 623/1.15 |
| 2004/0186551 A1 | 9/2004 | Kao | |
| 2005/0182480 A1 | 8/2005 | Doran et al. | |
| 2006/0235506 A1 * | 10/2006 | Ta et al. ....................... | 623/1.16 |
| 2007/0179590 A1 * | 8/2007 | Lu et al. ....................... | 623/1.16 |
| 2008/0114445 A1 * | 5/2008 | Melsheimer et al. ........ | 623/1.13 |

FOREIGN PATENT DOCUMENTS

| | | |
|---|---|---|
| EP | 0808614 | 11/1997 |
| WO | 97/18006 A1 | 5/1997 |
| WO | 97/25937 A1 | 7/1997 |
| WO | WO 99/43272 | 9/1999 |
| WO | 0028922 | 5/2000 |
| WO | WO 2006/034062 | 3/2006 |
| WO | WO 2008/030488 | 3/2008 |
| WO | WO 2008/051543 | 5/2008 |
| WO | PCT/US2009/005997 | 2/2010 |
| WO | 2010030928 A1 | 3/2010 |
| WO | PCT/US09/005997 | 7/2010 |

* cited by examiner

*Primary Examiner* — David H Willse
*Assistant Examiner* — Tiffany Shipmon
(74) *Attorney, Agent, or Firm* — Richard J. Godlewski

(57) ABSTRACT

A rotationally-symmetric stent graft for deploying in a curved vessel has identical spaced stents along its length, with the stents being further apart in the region of the greatest curvature. The ends of the stents are parallel to each other and to the ends of the graft. The inter-stent spacing may vary along the entire length of the graft or only adjacent one end.

20 Claims, 2 Drawing Sheets

STENT MEMBER

CROSS-REFERENCE TO RELATED APPLICATIONS

This application claims priority of United Kingdom patent application number 0820360.6, filed Nov. 6, 2008.

TECHNICAL FIELD

The present invention relates to stent members, such as stent grafts, having a plurality of stents, sometimes referred to as stent sections, spaced along their length.

BACKGROUND ART

At present stent grafts are provided with a plurality of stent sections evenly spaced along the graft. The spacing between the stent sections allows the stent graft to be curved when inserted in a body vessel but still provides sufficient support to keep the vessel open for fluid flow.

US 2005/0182480 discloses a stent member having spaced undulating bands along its length, the bands being interconnected by longitudinal struts. The spacing between the bands at one or both ends of the stent member may differ from the spacing between the bands at the middle of the stent member.

WO 2008/051543 discloses a stent member designed to fit a curved body vessel in which parallel-sided stents are disposed along the length of the stent member. One side of the stent member is provided with buckled portions to permit it to expand when deployed. This requires the stent member to be oriented into the correct rotational portion before it is expanded into its final disposition.

U.S. Pat. No. 6,709,453 and U.S. Pat. No. 6,723,119 disclose stent members with alternating circumferential bands of different patterns of loops.

SUMMARY OF THE INVENTION

The present invention seeks to provide an improved stent member.

According to an aspect of the present invention, there is provided a stent member having a longitudinal extent and comprising a plurality of spaced and mutually-parallel stents, the ends of all the stents being perpendicular to the longitudinal extent of the stent member and the spacing between mutually-adjacent stents increasing monotonically in a direction from one end of the stent graft to the other.

Preferably, the stent member is substantially rotationally symmetrical.

The stents, or at least all the stents except one or both end stents, are substantially identical.

In preferred embodiments, the spacing between mutually-adjacent stents increases from one end of the stent member to the other end.

In other preferred embodiments, the spacing between mutually-adjacent stents is substantially uniform adjacent one end of the stent member, and increases from a central region of the stent member to the other end.

In preferred embodiments, the stents do not have mutually-interconnecting struts and are only connected by graft material.

BRIEF DESCRIPTION OF THE DRAWINGS

Preferred embodiments of the present invention will now be described, by way of example only, with reference to the accompanying drawings, of which.

DESCRIPTION OF THE PREFERRED EMBODIMENTS

Figure 1:
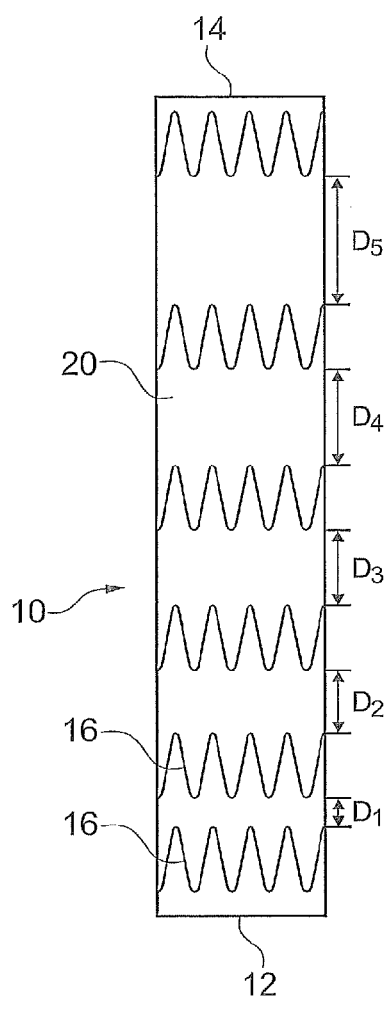
FIG. 1 shows a stent member according to a first embodiment of the present invention in an unconstrained condition.

Referring to the drawings, a stent graft 10 is shown in a straight configuration in which it can be mounted on and delivered by an introduction system. The stent graft 10 comprises a tubular piece of biocompatible graft material 20 defining a lumen 22 and having a first end 12 and second end 14. Separate stents 16 are provided along the length of the material 20. The stents are shown only schematically in the Figures and may be self expanding z-stents made of stainless steel or shape memory material, such as Nitinol.

Starting from end 12 of the graft the spacing between adjacent stents 16 steadily increases so that, the following inequalities apply:

$$D_1 < D_2 < D_3 < D_4 < D_5$$

This has the advantage that the stents provide the overall amount of support which the graft requires, while permitting greater curvature of the part of the graft adjacent to end 14.

Figure 2:
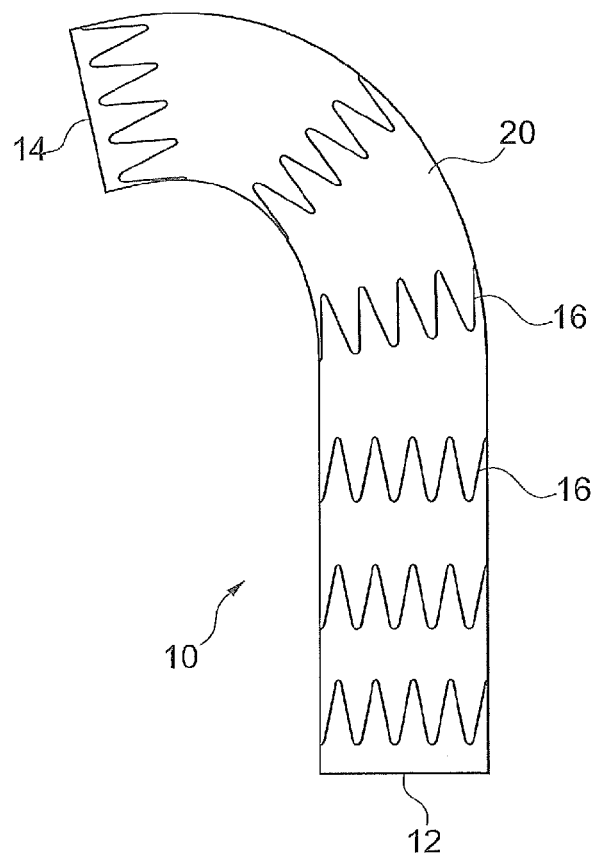
FIG. 2 shows the stent member of FIG. 1 in a curved configuration.

In use, the graft 20 is deployed in a curved body vessel in which case it is constrained to adapt the configuration shown in FIG. 2. The graft is located with the part adjacent end 14 (which curves more easily) in the region of greatest curvature of the vessel. The part of graft 20 adjacent end 12 is located in a region with less curvature.

Thus there is provided a stent graft with parts which can be curved to different extents while still providing a substantial stent coverage. The improved flexibility of end 14 avoids it becoming misaligned in the curved body vessel.

The above-described arrangement has several advantages. In particular, since it is rotationally-symmetric about its longitudinal axis, its deployment is simple; there are no problems in orienting it correctly once it has reached its desired location along the aorta since it can curve identically in all directions. Since the stents 16 are identical, the arrangement is cheaper and simpler to manufacture, and any of the stents can be attached to any location along the graft. The size of the stent graft and the spacing of the stents can be selected as desired so that the graft can be customised for a particular application.

In one preferred arrangement, the distance between adjacent stents increases regularly so that:

$$D_5 = D_4 + d = D_3 + 2d = D_2 + 3d = +4d$$

where d is a fixed distance.

Thus in a stent member of diameter 22 mm, $D_1$ can be 4 mm and d can be 1 mm, so that $D_5$ is 8 mm. For a stent member of diameter 46 mm, $D_1$ can be 8 mm and d can be 1.75 mm, so that $D_5$ is 15 mm. In other arrangements, the distance between adjacent stents may increase in irregular manner provided the relationship $$D_1 < D_2 < D_3 < D_4 < D_5 \text{ is maintained.}$$

The increases nearer end 12 may be smaller and, instead of monotonically increasing, may even be zero such that;

$$D_1 = D_2 = D_3$$

Here, as above, D4 may be equal to D3+d and D5 may be equal to D3+2d, where d is a fixed distance. In other arrangements, the distance corresponding to D5–D4 may be greater than the distance corresponding to D4–D3.

Figure 3:
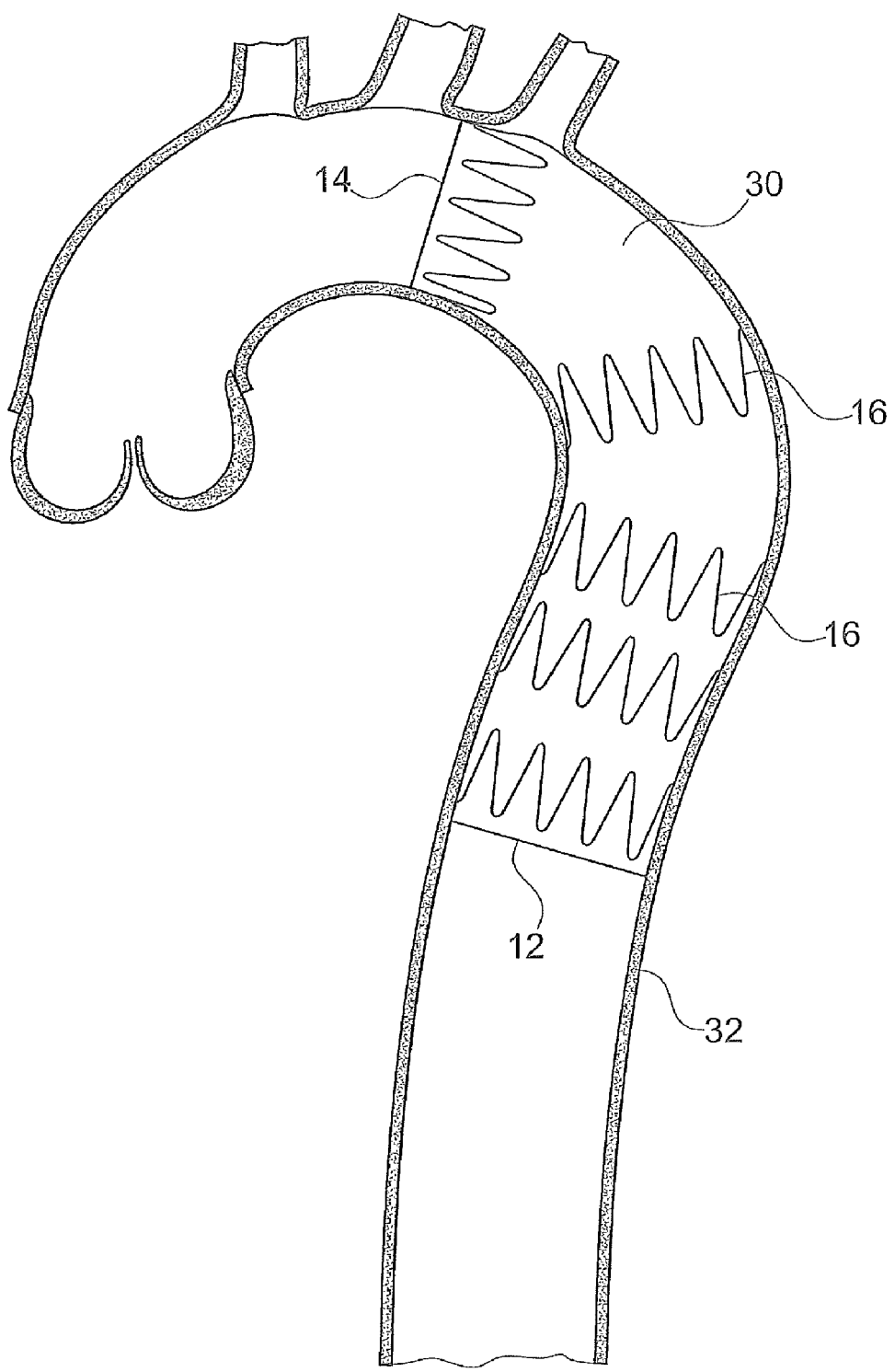
FIG. 3 shows the stent member according to a second embodiment of the present invention deployed into the thoracic arch and descending aorta of a patient.

FIG. 3 shows a stent graft 30 deployed in the thoracic arch and descending aorta 32 of a patient. The arch has a variable curvature and the part of the stent graft adjacent end 14 is located in the region of the greatest curvature. The other part of the graft adjacent end 12 is only slightly curved and may be substantially straight.

The spacings between the stents depend on various factors such as the diameter of the stent graft, and the materials of the stents 16 and the graft material 20. The diameter of the graft preferably lies between 22 and 46 mm. D, lies in the range 3 to 9 mm, preferably 4 to 8 mm. $D_5$ lies in the range 6 to 18 mm, preferably 8 to 15 mm. The spacings d lie in the range 0.5 to 2.5 mm, preferably 1.0 to 1.75 mm.

The stent graft may be applied to vessels other than the aortic arch and which have uneven curvature.

The stent graft may have an extra stent at one or each end which does not fall into the specific pattern of the other stents. Such extra stents may be provided with barb elements for attachment to the body vessel walls. In addition, the extra stents may be shorter than the other stents.

Some or all of the stents may be interconnected by struts if desired.

Instead of being self-expanding, the stents may be balloon-expandable. The stent graft may be provided with one or more fenestrations to permit communication with side vessels extending from a main body vessel.

The features of the various embodiments described above and their modifications may be substituted for or combined with one another as desired. It is also to be understood that the various features of the dependent claims appended hereto may be used with one another in any desired combination of those claims.

The invention claimed is:

1. A stent member having a longitudinal extent and comprising a plurality of spaced and mutually-parallel stents, the ends of all the stents being perpendicular to the longitudinal extent of the stent member and the spacing between at least four mutually-adjacent stents increasing monotonically in a direction from one end of the stent member to another.

2. A stent member according to claim 1 and which is substantially rotationally symmetric.

3. A stent member according to claim 2 wherein the stents are substantially identical.

4. A stent member according to claim 1 wherein the stents are substantially identical.

5. A stent member according to claim 1 wherein the plurality of spaced and mutually-parallel stents are separate stents.

6. A stent member having a longitudinal extent and comprising a plurality of spaced and mutually-parallel stents, the ends of all the stents being perpendicular to the longitudinal extent of the stent member and the spacing between at least four mutually-adjacent stents increasing monotonically in a direction from one end of the stent member to another, wherein the increase in the spacing between mutually-adjacent stents itself increases in regular manner, whereby the increase in the spacing from one stent to the next stent is constant.

7. A stent member according to claim 6 wherein the stents are substantially identical.

8. A stent member according to claim 6 and which is substantially rotationally symmetric.

9. A stent member according to claim 8 wherein the stents are substantially identical.

10. A stent member according to claim 6 wherein the plurality of spaced and mutually-parallel stents are separate stents.

11. A stent member having a longitudinal extent and comprising a plurality of spaced and mutually-parallel stents, the ends of all the stents being perpendicular to the longitudinal extent of the stent member, wherein the spacing between mutually-adjacent stents is substantially uniform adjacent one end of the stent member and the spacing between at least four mutually-adjacent stents increases monotonically in a direction from a central region of the stent member to the other end.

12. A stent member according to claim 11 wherein the stents are substantially identical.

13. A stent member according to claim 11 and which is substantially rotationally symmetric.

14. A stent member according to claim 13 wherein the stents are substantially identical.

15. A stent member according to claim 11 wherein the increase in the spacing between mutually-adjacent stents itself increases in regular manner, whereby the increase in the spacing from one stent to the next stent is constant.

16. A stent member according to claim 15 wherein the stents are substantially identical.

17. A stent member according to claim 15 and which is substantially rotationally symmetric.

18. A stent member according to claim 17 wherein the stents are substantially identical.

19. A stent member according to claim 11 wherein the plurality of spaced and mutually-parallel stents are separate stents.

20. A stent member according to claim 1 in the form of a stent graft with graft material connecting the stents.

* * * * *